(12) United States Patent
Callan et al.

(10) Patent No.: US 7,862,530 B2
(45) Date of Patent: Jan. 4, 2011

(54) HIGH CITRATE DIALYSATE AND USES THEREOF

(75) Inventors: Robin Callan, Bellevue, WA (US); James J. Cole, Arlington, WA (US)

(73) Assignee: Advanced Renal Technologies, Bellevue, WA (US)

( * ) Notice: Subject to any disclaimer, the term of this patent is extended or adjusted under 35 U.S.C. 154(b) by 430 days.

(21) Appl. No.: 10/984,374

(22) Filed: Nov. 8, 2004

(65) Prior Publication Data

US 2005/0119598 A1 Jun. 2, 2005

Related U.S. Application Data

(62) Division of application No. 09/667,489, filed on Sep. 22, 2000, now abandoned.

(60) Provisional application No. 60/155,514, filed on Sep. 22, 1999.

(51) Int. Cl.
*A61M 37/00* (2006.01)
*B01D 11/00* (2006.01)
*B01D 61/00* (2006.01)
*C02F 1/44* (2006.01)

(52) U.S. Cl. ............ 604/5.01; 604/4.01; 210/645; 210/646

(58) Field of Classification Search .......... 604/4.01, 604/5.01, 5.04, 6.01; 210/641, 645, 646
See application file for complete search history.

(56) References Cited

U.S. PATENT DOCUMENTS

| | | | | |
|---|---|---|---|---|
| 3,962,075 A * | 6/1976 | Fialkoff et al. | ............ | 210/641 |
| 4,339,433 A | 7/1982 | Kartinos et al. | ............ | 424/78 |
| 4,451,454 A * | 5/1984 | Wong | ............ | 424/717 |
| 4,500,309 A | 2/1985 | Diederich et al. | ............ | 604/5 |
| 4,581,141 A | 4/1986 | Ash | ............ | 210/502 |
| 4,661,246 A | 4/1987 | Ash | ............ | 210/87 |
| 4,663,166 A | 5/1987 | Veech | ............ | 424/146 |
| 4,756,838 A | 7/1988 | Veltman | ............ | 252/1 |
| 4,784,495 A | 11/1988 | Jonsson et al. | ............ | 366/151 |
| 4,879,280 A | 11/1989 | Seyffart et al. | ............ | 514/53 |
| 4,886,789 A | 12/1989 | Milner | ............ | 514/60 |
| 4,906,616 A | 3/1990 | Gilchrist et al. | ............ | 514/21 |
| 4,938,873 A | 7/1990 | Rossi | ............ | 210/646 |
| 5,032,615 A * | 7/1991 | Ward et al. | ............ | 514/574 |
| 5,108,767 A | 4/1992 | Mulchandani et al. | ............ | 426/72 |
| 5,252,213 A | 10/1993 | Ahmad et al. | ............ | 210/542 |
| 5,474,992 A | 12/1995 | Ogata et al. | ............ | 514/100 |
| 5,589,197 A | 12/1996 | Shockley et al. | ............ | 424/663 |
| 5,591,344 A | 1/1997 | Kenley et al. | ............ | 210/636 |
| 5,624,668 A | 4/1997 | Lawrence et al. | ............ | 424/78.17 |
| 5,645,734 A | 7/1997 | Kenley et al. | ............ | 210/805 |
| 5,651,893 A | 7/1997 | Kenley et al. | ............ | 210/636 |
| 5,658,456 A | 8/1997 | Kenley et al. | ............ | 210/85 |
| 5,674,390 A | 10/1997 | Matthews et al. | ............ | 210/261 |
| 5,674,404 A | 10/1997 | Kenley et al. | ............ | 210/741 |
| 5,690,821 A | 11/1997 | Kenley et al. | ............ | 210/195.1 |
| 5,698,100 A | 12/1997 | Levin et al. | ............ | 210/321.6 |
| 5,728,678 A | 3/1998 | Trimbo et al. | ............ | 514/12 |
| 5,762,782 A | 6/1998 | Kenley et al. | ............ | 210/85 |
| 5,780,438 A | 7/1998 | Gilchrist et al. | ............ | 514/21 |
| 5,783,072 A | 7/1998 | Kenley et al. | ............ | 210/195.2 |
| 5,827,820 A | 10/1998 | duMoulin et al. | ............ | 514/2 |
| 5,851,483 A | 12/1998 | Nicolle et al. | ............ | 422/28 |
| 5,906,978 A | 5/1999 | Ash | ............ | 514/23 |
| 5,945,129 A | 8/1999 | Knerr et al. | ............ | 424/676 |
| 6,019,925 A | 2/2000 | Diamantoglou et al. | ............ | 264/203 |
| 6,077,836 A | 6/2000 | Milner | ............ | 514/54 |
| 6,610,206 B1 | 8/2003 | Callan et al. | ............ | 210/646 |
| 6,779,468 B1 | 8/2004 | Gupta | ............ | 110/647 |
| 2004/0060865 A1 | 4/2004 | Callan et al. | ............ | 210/646 |

FOREIGN PATENT DOCUMENTS

| | | |
|---|---|---|
| DE | 41 14 908 | 11/1992 |
| DE | 196 54 746 | 7/1998 |
| EP | 0 022 922 A1 | 1/1981 |
| EP | 457 960 A2 | 11/1991 |
| EP | 0 564 672 A1 | 10/1993 |
| EP | 821 951 A1 | 2/1998 |

(Continued)

OTHER PUBLICATIONS

Abstract of DE 196 54 746, Jul. 2, 1998, esp@cenet database.

(Continued)

*Primary Examiner*—Melanie J Hand
(74) *Attorney, Agent, or Firm*—Seed IP Law Group PLLC

(57) ABSTRACT

The dose of dialysis in terms of urea clearance is marginal in many hemodialysis patients, and metabolic acidosis as determined by the pre-dialysis serum $HCO_3$ level is common. A dialysate that included citric acid rather than acetic acid as acidifying agent provides superior performance properties. Citrate-containing dialysate was used exclusively in 22 hemodialysis patients. Initially, only 8 of the 22 patients had a pre-dialysis serum $HCO_3 > 23$ mEq/L (lower limit of normal), however, after 12 weeks of dialysis using the citrate-containing dialysate, the serum $HCO_3$ normalized in 15 patients (p=0.0001, Chi-square). Dialysis variables were kept constant in 19 of the patients, who also used and reused the same dialyzer model throughout. In these patients, the initial average urea reduction ratio (URR) was 68.5±5.9%, and after treatment with the citrate dialysate disclosed herein, this ratio had increased to 73±5.3% (p<0.03). SpKt/V, calculated using the Daugirdas II formula, also increased from 1.23±0.19 to 1.34±0.2 (p=0.01). This increased urea clearance may be the result of the anticoagulant property of citrate maintaining patency of the dialyzer membrane. The increase in pre-dialysis serum $HCO_3$ may represent increased delivery from the dialysate and production from citric acid.

27 Claims, 3 Drawing Sheets

FOREIGN PATENT DOCUMENTS

| | | |
|---|---|---|
| EP | 1 059 083 A2 | 12/2000 |
| JP | 8-92070 | 4/1996 |
| JP | 10-87478 A | 4/1998 |
| WO | WO 92/11046 | 7/1992 |
| WO | WO 9211046 A1 * | 7/1992 |
| WO | WO 96/01118 | 1/1996 |
| WO | WO 98/06482 A1 | 2/1998 |
| WO | WO 98/29151 A1 | 7/1998 |
| WO | WO 98/29434 A1 | 7/1998 |
| WO | WO 99/07419 A1 | 2/1999 |

OTHER PUBLICATIONS

Abstract of DE 41 14 908, Nov. 12, 1992, esp@cenet database.

J. Van Der Meulen et al., "Citrate anticoagulation and dialysate with reduced buffer content in chronic hemodialysis," *Clinical Nephrology* 37(1): 36-41, 1992.

Morishita Roussel KK, "Agent for blood dialysis—comprises electrolytes contg. sodium, calcium, chloride and hydrogen-carbonate ions," *Derwent World Patent Index*, Accession No. 235949, 1996. Abstract for JP 8-092070.

Ahmad et al., "Increased Dialyzer Efficiency Using a Dialysate Containing Citric Acid in Place of Acetic Acid," *J. Am. Soc. Nephrol.* 10: 188A, Abstract A0961, 1999.

Ahmad et al., "Effect of the Normalization of Acid-Base Balance on Postdialysis Plasma Bicarbonate," *Trans. Am. Soc. Artif. Intern. Organs* 26: 318-321, 1980.

Apsner et al., "A Simple Method for Citrate Anticoagulation (CA) during High Flux Dialysis: Experience with 760 Dialyses in 34 Patients," *J. Am. Soc. Nephrol.* 10: 188A, Abstract A0962, 1999.

Brady and Hasbargen, "Correction of Metabolic Acidosis and Its Effect on Albumin in Chronic Hemodialysis Patients," *Am. J. Kid. Dis.* 31(1): 35-40, Jan. 1998.

Drukker et al., *Replacement of Renal Function by Dialysis*, Fourth Edition, Kluwer Academic Publishers, Dordrecht, The Netherlands, 1996, p. 345.

Dzik and Kirkley, "Citrate Toxicity During Massive Blood Transfusion," *Transfusion Medicine Reviews* 2(2): 76-94, Jun. 1988.

European Pharmacopoeia Commission, "Peritoneal Dialysis, Solutions For," in *European Pharmacopoeia*, 3$^{rd}$ edition, Strasbourg, Germany, Council of Europe, 1997, pp. 1301-1303.

Golberg, "Pharmacology of Parenteral Iron Preparations," in Wallerstein and Mettier (eds.), *Iron in Clinical Medicine*, University of California Press, Berkeley and Los Angeles, 1958, pp. 74-92.

Guest et al., "Functional consequences of correction of metabolic acidosis in hemodialysis patients," *J. Am. Soc. Nephrol.* 8: 236A, Abstract No. A1090, Sep. 1997.

Jander and Blasius, *Lehrbuch der analytischen and präparativen anorganischen Chemie* (translated *Text book of analytical and preparative inorganic chemistry*), S. Hirzel Verlag Stuttgart, Germany, 1973, 10$^{th}$, revised edition, Chapter 2.6.5.5.4, "Buffer Capacity," p. 66, translation.

Lin et al., "Influence of Rapid Correction of Metabolic Acidosis on Serum Osteocalcin Level in Chronic Renal Failure," *Asaio Journal* 40: M440-M444, 1994.

Reaich et al., "Correction of acidosis in humans with CRF decreases protein degradation and amino acid oxidation," *Am. J. Physio.* 7: E230-E235, 1993.

Sonikian et al., "Potential Effect of Metabolic Acidosis on β2—Microglobulin Generation: in Vivo and in Vitro Studies," *J. Am.Soc. Nephrol.* 7(2): 350-356, 1996.

Suh and Wadhwa, "Iron Dextran Treatment in Peritoneal Dialysis Patients on Erythropoietin," *Adv. Perit. Dial.* 8: 464-466, 1992.

Wu et al., "Clinical application of EPO and chalybeate," *Journal of Postgraduates of Medicine* 24(4): 50-52, Apr. 2001, with English translation.

Yu et al., "Discussion on application of zinc-containing dialysate in hemodialysis patients," *Chinese Journal of Renal Diseases* 11(5): 281, Oct. 1995, with English translation.

Caruana and Keep, "Anticoagulation," in John T. Daugirdas, M.D. and Todd S. Ing, M.D. (eds.), *Handbook of Dialysis*, Little, Brown and Company, 1994, pp. 121-135.

Flanigan et al., "Regional Hemodialysis Anticoagulation: Hypertonic Tri-Sodium Citrate or Anticoagulant Citrate Dextrose-A," *American Journal of Kidney Diseases* 27(4): 519-524, Apr. 1996.

Kossmann et al., 55% Heparin Reduction Using Citrate Dialysate (Citrasate®), http://www.dialmedsupply.com/citrasate/PDF/HeparinReduction.pdf, download date Nov. 24, 2009.

Perdrix et al., "Anticoagulation régionale par le citrate au cours de l'hémodialyse chez les patients á haut risque hémorragique," *Ann. Fr. Anesth. Réanim.* 7: 31-35, 1988.

Pinnick et al., "Regional Citrate Anticoagulation for Hemodialysis in the Patient at High Risk for Bleeding," *The New England Journal of Medicine* 308(5): 258-261, Feb. 3, 1983.

Šrámek et al., "Continuous venovenous hemodiafiltration (CVVHDF) with citrate anticoagulation in the treatment of a patient with acute renal failure, hypercalcemia, and thrombocytopenia," *Intensive Care Med* 24: 262-264, 1998.

Zawada, Jr. et al., "Indications for Dialysis," in John T. Daugirdas, M.D. and Todd S. Ing, M.D. (eds.), *Handbook of Dialysis*, Little, Brown and Company, 1994, pp. 3-9.

Citrasate® Additive Chart, http://www.dialmedsupply.com/citrasate/PDF/Citrasate_Additives.pdf, download date Nov. 24, 2009.

* cited by examiner

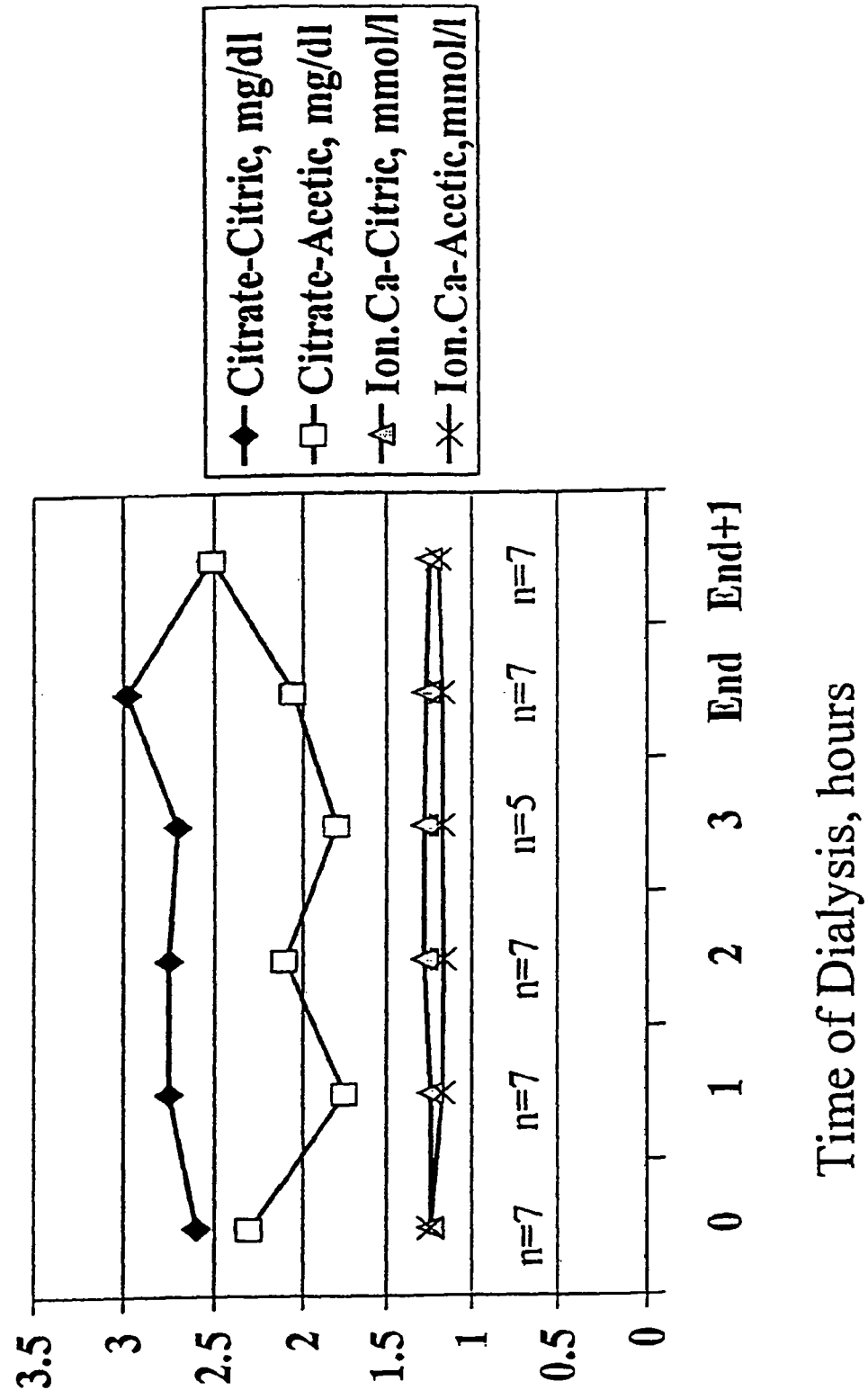
Figure 1: Serum citrate and ionized calcium concentrations during and one hour post-dialysis using citrate and acetic acid dialysate in 7 patients. (Two patients had shorter dialysis time than other five.)

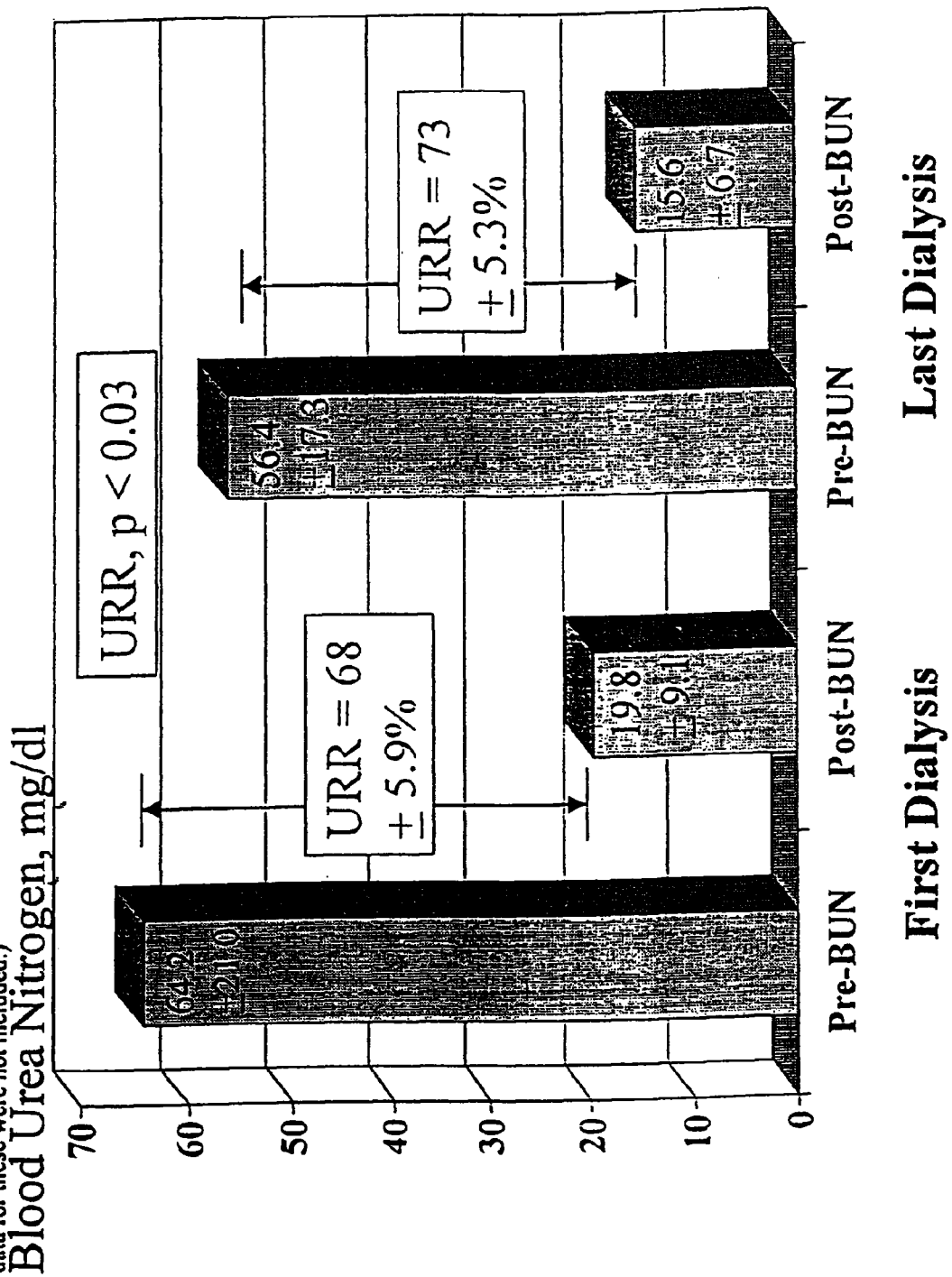
Figure 2: Pre- and post-dialysis blood nitrogen concentrations for the first and the last dialysis of Exclusive Use study in 19 patients using citrate dialysate. Calculated urea reduction ratios are also shown for these dialyses. (In three patients dialyzer changed during the study and data for these were not included.)

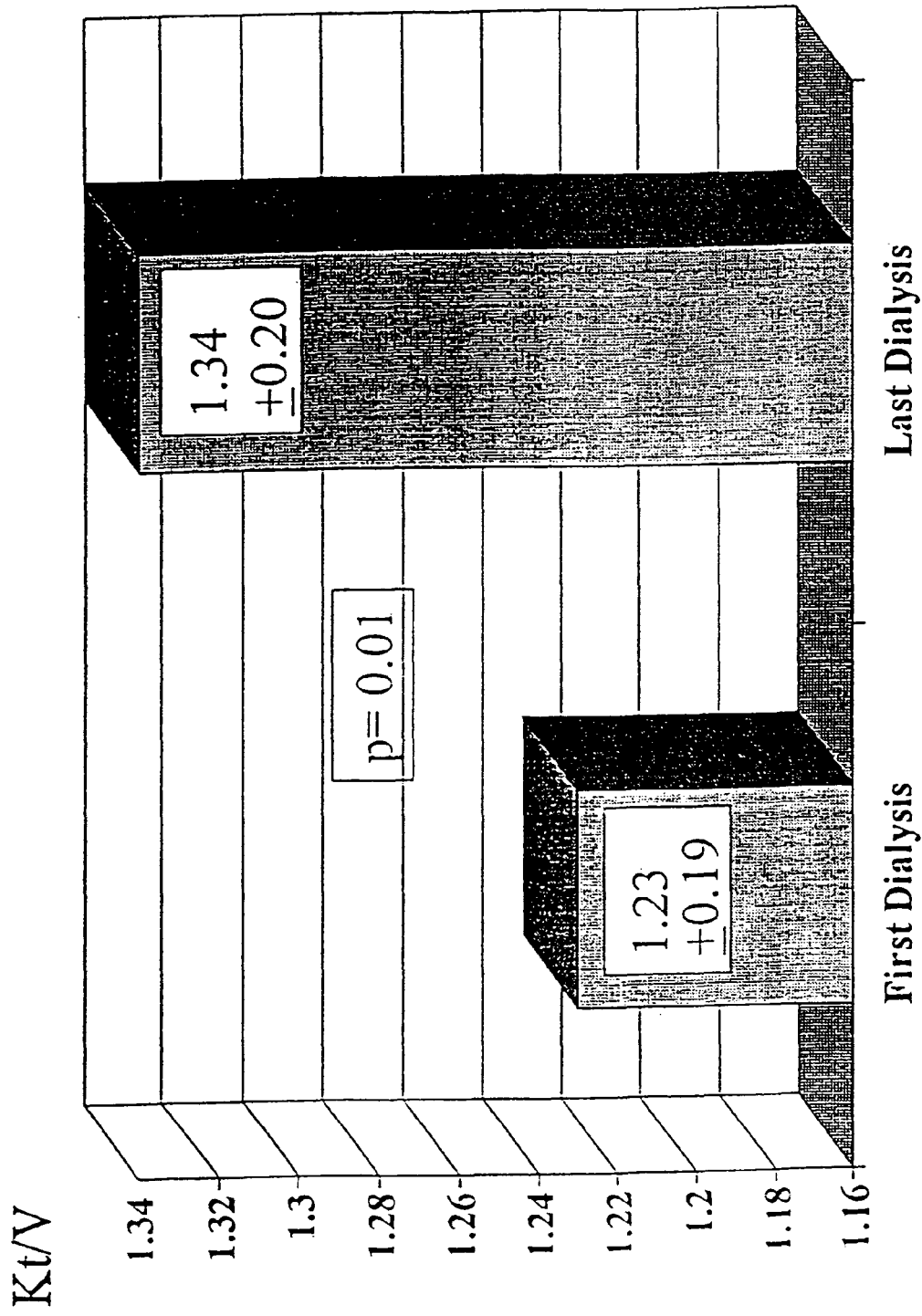
Figure 3: Delivered Kt/V calculated by Daugirdas formula for the first and last dialysis of the Exclusive Use study in 19 patients using citrate dialysate.

HIGH CITRATE DIALYSATE AND USES THEREOF

CROSS-REFERENCE TO RELATED APPLICATION

This application is a divisional application of U.S. application Ser. No. 09/667,489, filed Sep. 22, 2000 (now pending), which claims priority to U.S. Provisional Application No. 60/155,514, filed on Sep. 22, 1999; both of which applications are incorporated herein by reference in their entireties.

TECHNICAL FIELD

The present invention relates generally to dialysis, and more specifically to citrate-containing dialysate and uses thereof in dialysis.

BACKGROUND OF THE INVENTION

Kidneys are essentially blood cleansing organs. A person's kidneys serve several vital functions, including the removal of waste from the body in the form of urine; filtration of toxins from the blood; and providing an appropriate concentration of some important nutrients, including potassium and calcium, in the blood. To achieve these functions, an artery from the heart brings blood into the kidneys, where the blood is passed through, and is cleaned by, a network of millions of tiny units called nephrons. The nephrons filter out toxins, excess nutrients and body fluid and excrete them in the form of urine into the bladder. After being cleaned and filtered, the blood passes from the kidneys, through veins, and back into circulation.

For those instances when a person's kidneys don't function properly, a process called dialysis has been developed and is in widespread use. Essentially, dialysis artificially replaces the functions of the kidney. There are two distinct types of dialysis: hemodialysis and peritoneal dialysis. Hemodialysis involves removing blood from the body and filtering it in a machine. The patient is connected by a tube to the dialysis machine, which continuously draws blood out of the patient, and then contacts that blood with a membrane in a dialyzer. The other side of the membrane contains a continuously circulating aqueous solution called dialysate. Excess fluid and toxins flow from the blood, through the membrane, and into the dialysate, thereby cleansing the blood. Salts and other nutrients may pass from the dialysate, through the membrane and into the blood. After passing through the dialyzer, the cleansed blood is returned to the patient. For many patients, hemodialysis is performed for 3 to 4 hours at least three times a week. It is usually performed at a dialysis center, although home dialysis is also possible.

Peritoneal dialysis is also known as internal or in-body dialysis. Like hemodialysis, peritoneal dialysis entails the use of a blood-cleansing solution called dialysate; the composition of a dialysate for peritoneal dialysis is typically different from the composition of dialysate for hemodialysis. In peritoneal dialysis, dialysate is infused into the peritoneal cavity (the region of the abdomen that is lined by the peritoneum). While in the peritoneal cavity, the dialysate functions to extract toxins and excess fluid from the blood. After a period of time, the solution is drained from the body cavity, taking with it the undesired toxins and excess fluid.

Further information regarding dialysis and kidney function may be obtained through, for example, the American Society of Nephrology (www.asn-online.com, Washington, D.C.).

The present invention identifies and solves problems with existing dialysis, identifies new opportunities for dialysis, and provides further related advantages as disclosed more fully herein.

BRIEF DESCRIPTION OF THE DRAWINGS

FIG. 1 is a plot of time of dialysis (hours) vs. the serum concentration of citrate and ionized calcium during and one hour post-dialysis using citrate and acetic acid dialysate in 7 patients. (Two patients had shorter dialysis time than other five.)

FIG. 2 is a bar chart of pre- and post-dialysis blood urea nitrogen concentrations for the first and the last dialysis of the Exclusive Use study described herein, for 19 patients using citrate dialysate. Calculated urea reduction ratios are also shown for these dialyses. (In three patients the type of dialyzer was changed during the study. Data from these three were not included.)

FIG. 3 is a bar chart of delivered Kt/V calculated by Daugirdas formula for the first and last dialysis of the Exclusive Use study in 19 patients using citrate dialysate.

DETAILED DESCRIPTION OF THE INVENTION

In one aspect, the present invention provides dialysate compositions having high concentrations of citrate. In another aspect, the present invention provides methods of performing dialysis with such dialysate compositions, in order to provide unexpected benefits. Thus, the present invention provides for increasing the amount of citrate in dialysate to increase and create treatment benefits associated with its use.

All current dialysate formulations include an acid to achieve a proper pH, where that pH is typically a physiological pH of about 7.4. The present invention recognizes that there is a significant benefit to the use of citrate in dialysate, above and beyond the benefit provided by using citric acid as a pH-adjusting component of dialysate. Indeed, the present invention recognizes that dialysate may be used to provide benefits above and beyond the function of providing a normalizing of certain of the patient's blood constituent concentrations.

As described in more detail herein, a citrate concentration of 2.4 mEq/L in dialysate was studied for its effect on the dialysis process, relative to the use of acetic acid. This concentration was selected because increasing the citrate level above 2.4 mEq/L has traditionally led to clinically unacceptable decreases in ionized calcium within the patient's blood. The present invention recognizes that citrate levels of greater than 2.4 mEq/L may be successfully employed in dialysate, when compensatory action is taken, and that such a high citrate dialysate may provide unexpected and desirable advantages in dialysis treatment.

For example, although a dialysate citrate concentration of 2.4 mEq/L is well below the level needed to achieve systemic anti-coagulation, this and higher concentrations has been surprisingly found to provide an anti-coagulation effect at the point of blood/dialysate interaction, i.e., the pore openings of the dialyzer. This surprising effect is associated with surprising benefits, which include increasing the treated patient's 'Dose of Dialysis;' and increasing the ability to reuse dialyzers.

Furthermore, the high citrate dialysate of the present invention provides additional surprising and advantageous effects, which are particularly pertinent to certain patients undergoing dialysis. Thus, in one aspect of the present invention, the high citrate dialysate is particularly beneficial in treating patients with chronic acidosis, in order to reduce the acidity of their blood. In another aspect, the high citrate dialysate is particularly useful in instances where patients should be heparin-free during dialysis. For example, post-operative patients may undergo acute kidney failure due to the kidney's response to the anesthesia, and thereafter need dialysis treatment until kidney recovery occurs. Heparin or other anti-coagulant should not be delivered systemically to these patients because retaining the patient's ability to clot blood is an important part of the healing process. With traditional dialysate, undesirable blood clotting will occur within the dialyzer, unless the patient receives some anti-coagulant. However, with the high citrate dialysate of the present invention, a patient with acute kidney failure can undergo successful dialysis without systemic administration of anti-coagulant. A patient with acute kidney failure may also experience more rapid recovery of kidney function upon exposure to the high citrate dialysate of the present invention, in comparison to conventional dialysate, because the high citrate dialysate has less tendency to activate complement formation, where complement formation tends to slow down kidney recovery.

In one aspect, the present invention provides dialysate compositions having citrate at concentrations greater than or equal to 2.4 mEq/L, and possibly as high as 20 mEq/L. Preferably, the citrate concentration in the dialysate will be in the range of about 2.4 to 15 mEq/L, and more preferably within the range of 3 to 10 mEq/L. When dialysate having such high citrate concentration is used in dialysis, the impact on the patient's calcium levels should be addressed, and methods to address this issue are presented herein.

In one embodiment, the increased citrate that would enter the patient's blood as a consequence of using the high citrate dialysate is offset by including additional ionized calcium and magnesium in the dialysate, and optionally reducing the levels of sodium chloride and sodium bicarbonate in the dialysate. Thus, both the calcium and magnesium concentrations in the high citrate dialysate may be higher than the concentrations found in standard dialysate. The calcium ion concentration in a high citrate dialysate of the present invention may be as high as about 5 mEq/L, while the magnesium ion concentration in a high citrate dialysate of the present invention may be as high as about 2 mEq/L.

In an alternative embodiment, the dialysate entering the dialyzer, and contacting the patient's blood, contains a high level of citrate, but not a high level of either calcium or magnesium. When the calcium and/or magnesium ion concentration in dialysate is not increased to compensate for the calcium arid magnesium binding action of citrate, then the calcium ion concentration in the citrate may be as low as about 2.5 mEq/L, while the magnesium ion concentration may be as low as about 1.0 mEq/L.

If the high citrate dialysate does not contain compensatory levels calcium and/or magnesium ions, then the blood leaving the dialyzer will have a high concentration of citrate, and in fact may have a higher concentration of citrate than is clinically desirable, due to the tendency of the citrate to bind calcium within the patient. To address this consequence, in one method of the invention, calcium may be added directly to the blood, at a point after the blood leaves the dialyzer but before the blood re-enters the patient. In this way, the desirable effects of high citrate levels within the dialyzer are obtained, while obviating the undesirable effects of having high citrate levels within the blood that is, in turn, within the patient.

The calcium may be added to the patient's blood in the form of an aqueous solution of calcium chloride, to thereby effectively neutralize the calcium binding effect of the citrate. Using this approach, a patient that is prone to undesirable clotting may receive dialysis without the need to receive an injection or other direct administration of an anti-coagulant. In a preferred method, the patient undergoing the dialysis does not have a high level of heparin within the patient's blood during the time of dialysis. However, the patient may receive heparin, and then undergo dialysis with a high citrate dialysate, without adverse effects.

The incorporation of a high amount of citrate in a dialysate potentially causes another problem. Within the body, citrate decomposes to bicarbonate. Dialysate often contains bicarbonate, and accordingly a high citrate dialysate according to the present invention preferably contains a reduced amount of bicarbonate. Thus, the high citrate dialysate of the present invention may contain less sodium bicarbonate than traditional dialysate, and may contain at little as 25 mEq/L, or as much as about 40 mEq/L of sodium bicarbonate. The sodium chloride concentration in the high citrate dialysate may also be reduced to as little as about 110 mEq/L, or may be equal to about 140 mEq/L of sodium chloride.

The citrate in the present dialysis compositions may come from citric acid, as well as other sources of citrate, including a buffer such as trisodium citrate, as well as additives such as calcium and magnesium citrate. Thus, the concentration of citrate in a dialysate of the invention is not constrained by, or directed solely to, providing a proper pH for a dialysate, but instead is selected to provide additional benefits to the patient receiving the dialysate. Because incorporation of too much citric acid into the dialysate will cause a very low pH, it is preferred to use at least some citrate salt, e.g., trisodium citrate, as the source of citrate, in the dialysate compositions of the present invention.

As used herein, "citrate" refers to a citrate anion, in any form, including citric acid (citrate anion complexed with three protons), salts containing citrate anion, and partial esters of citrate anion. Citrate anion is an organic, tricarboxy-late with the following chemical formula:

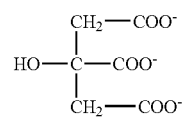

Citric acid, which has been assigned Registry No. 77-92-2 by the American Chemical Society, has the molecular formula $HOC(CO_2H)(CH_2CO_2H)_2$ and a formula weight of 192.12 g/mol. A citrate salt (i.e., a salt containing citrate anion) is composed of one or more citrate anions in association with one or more physiologically acceptable cations. Exemplary physiologically acceptable cations include, but are not limited to, protons, ammonium cations and metal cations. Suitable metal cations include, but are not limited to, sodium, potassium, calcium, and magnesium, where sodium and potassium are preferred, and sodium is more preferred. A composition containing citrate anion may contain a mixture of physiologically acceptable cations.

A partial ester of a citrate anion will have one or two, but not all three, of the carboxylate (i.e., —COO⁻) groups of citrate anion in an ester form (i.e., —COO—R, where R is an organic group). In addition to one or two R groups, the partial ester of a citrate anion will include one or two physiologically acceptable cations (so that the total of the R group(s) and cation(s) equals three). The R group is an organic group, preferably a lower alkyl.

The citrate is preferably in association with protons and/or metal cations. Exemplary of such citrate compounds are, without limitation, citric acid, sodium dihydrogen citrate, disodium hydrogen citrate, trisodium citrate, trisodium citrate dihydrate, potassium dihydrogen citrate, dipotassium hydrogen citrate, calcium citrate, and magnesium citrate. In one embodiment, the citrate is present in the dialysate precursor composition in the form of one or more of citric acid, sodium dihydrogen citrate, disodium hydrogen citrate, potassium dihydrogen citrate, or dipotassium hydrogen citrate.

In a preferred embodiment, citric acid provides the source for the citrate anions. In this embodiment, the citric acid functions as the main acidifying agent of the precursor composition. Citric acid is a relatively inexpensive physiological acid that, under ambient conditions, is in the form of a dry chemical powder, crystal, pellet or tablet. Any physiologically tolerable form of citric acid may be used to introduce citrate anions to the composition. For instance, the citric acid may be in the form of a hydrate, including a monohydrate.

In the event that the pH of a high citrate dialysate begins to increase (i.e., the dialysate becomes more basic) during the course of a dialysis treatment, a buffering anion, present in an effective amount, may be used to prevent the pH of the dialysate composition from rising beyond a physiologically acceptable range. For compositions having the citrate concentrations described above, and to provide the desired buffering effect, the dialysate composition may contain from about 0.001 to about 4 mEq/L of acetate and/or lactate. In a preferred embodiment, the dialysate may contain from about 0.01 to about 2.5 mEq/L of acetate and/or lactate. In one embodiment, the buffering anion is a mixture of acetate and lactate. In another embodiment, the buffering anion is acetate, and lactate is not present in the composition. In another embodiment, the buffering anion is lactate, and acetate is not present in the composition.

With peritoneal dialysate, to facilitate the diffusion between blood and dialysate, it is desirable to maintain an osmotic gradient between the fluids by adding an osmotic agent to the dialysate. The presence of an osmotic agent in the peritoneal dialysate will encourage excess fluid and metabolic waste byproducts to flow from the blood and into the dialysate. A suitable osmotic agent for the precursor dialysate composition is sugar. The sugar is preferably selected from glucose (e.g., dextrose), poly(glucose) (i.e., a polymer made from repeating glucose residues, e.g., icodextrin, made from repeating dextrose units), or fructose. While it is possible to make a dialysate precursor with no sugar, if sugar is to be added to the dialysate composition, it is generally dextrose. It is further appreciated that any biocompatible, non-sugar osmotic agent that functions as an equivalent could be a viable substitute. The sugar is typically present in the dialysate composition at a concentration of less than about 60 g/L.

A patient's blood serum contains several components including, for example, proteins, carbohydrates, nucleic acids, and various ions. Typically, a dialysate composition prescribed by a physician is chosen to reduce, increase, or normalize the concentration of a particular component in the serum. Any of these components may be added to a high citrate dialysate of the present invention.

As used herein, "mEq/L" refers to the concentration of a particular dialysate component (solute) present in proportion to the amount of water present. More specifically, mEq/L refers to the number of milli-equivalents of solute per liter of water. Milli-equivalents per liter are calculated by multiplying the moles per liter of solute by the number of charged species (groups) per molecule of solute, which is then multiplied by a factor of 1,000. As an example, when 10 grams of citric acid are added to a liter of water, the citric acid is present at a concentration of 10 g/L. Anhydrous citric acid has a molecular weight of 192.12 g/mol; therefore, the number of moles per liter of citric acid, and consequently citrate anion (since there is one mole of citrate anion per mole of citric acid), is 10 g/L divided by 192.12 g/mol, which is 0.05 mol/L. Citrate anion has three negatively charged species in the form of carboxylate groups. Accordingly, the citrate concentration of 0.05 mol/L is multiplied by three and then by 1,000, in order to provide a concentration of citrate in terms of mEq/L, which in the present example is 156 mEq/L of citrate anion.

A preferred water of the invention is water that has been treated in order that it is essentially pyrogen-free and at least meets the purity requirements established by the Association for the Advancement of Medical Instrumentation (AAMI) for dialysate compositions. The water may also be referred to as treated water or AAMI-quality water. A monograph describing water treatment for dialysate, monitoring of water treatment systems, and regulation of water treatment systems is available from AAMI (Standards Collection, Volume 3, Dialysis, Section 3.2 Water Quality for Dialysis, 3 ed., 1998, AAMI, 3330 Washington Boulevard, Arlington, Va. 22201) or through the Internet at http://www.aami.com. In addition, all of the other components of the precursor dialysate composition of the present invention are preferably at least United States Pharmacopeia (USP)-grade purity, which is generally a purity of about 95%.

The benefits attendant to the use of citrate in dialysate flow, in part, from the anti-coagulation properties of citrate. The present dialysate compositions emphasize, and take advantage of, localized anti-coagulant properties of citrate, to achieve benefits including: increasing the blood flow through the dialyzer, thereby increasing the dose of dialysis; keeping the dialyzer cleaner, thereby allowing more extended reuse of the dialyzer; mitigating the clogging of dialyzer pores, thereby allowing greater clearance of 'middle molecules' e.g., molecules having a molecular weight of about 12,000 Daltons; providing a significant source of additional bicarbonate to the blood, thereby reducing the incidence of chronic acidosis; and reducing or eliminating the need for the anti-coagulant Heparin.

In addition to the benefits arising from maximizing, and taking advantage of the anti-coagulant properties of citrate, other potential and realized benefits of using higher levels of citrate in dialysate include increasing patient metabolism and achieving better management of calcium and magnesium levels. Currently, products such as calcium or magnesium salts, e.g., calcium acetate, are administered to patients in order to bind or sequester phosphate, and thereby lower the phosphate level in the patient's blood. However, these phosphate-binding agents concomitantly increase the calcium and/or magnesium concentration in blood, and in some instances this is undesirable. Because citrate will bind or sequester ionized calcium and/or magnesium, the high citrate dialysate of the present invention may be used in conjunction with phosphate binding agents, in order to achieve better management of phosphate levels along with calcium and magnesium levels.

The indications for use of a new higher-citrate dialysate would include patients: with a risk of bleeding from the use of systemic anti-coagulation (Heparin); with an antibody to (intolerance to) Heparin; who only achieve limited dialyzer reuse due to extensive clotting within the dialyzer during dialysis; have chronic acidosis; and/or usually achieve less than a desirable 'Dose of Dialysis.'

The effects of the citric acid-containing dialysate of the present invention, and methods of using a citric acid-containing dialysate according to the present invention, are shown in the following studies. As described herein, the anti-coagulation properties of citrate can be used to give patients a better dialysis treatment and decrease the cost of the treatment.

To summarize the studies, a dry dialysate concentrate acidified with citric acid (citrate dialysate) was used in two separate clinical studies with hemodialysis patients. The first study compared a single treatment using this dialysate with one dialysis using regular standard dialysate acidified with acetic acid (acetic acid dialysate) in a prospective, randomized, Crossover study of 74 dialyses. Changes in the blood levels of electrolytes and other blood constituents during dialysis were calculated by subtracting post-dialysis from pre-dialysis blood concentrations. Compared to acetic acid dialysate, citrate dialysate was associated with significantly greater decreases in total and ionized calcium, magnesium and chloride. Citrate dialysate was also associated with larger increases in serum sodium, and citrate concentrations, although their post-dialysis concentrations remained within or just outside normal ranges. Changes in other blood constituents were similar with both dialysates.

The second study used citrate dialysate exclusively for all dialyses over a twelve-week period in twenty-two patients (the study actually began with twenty-five patients, but three were dropped for various reasons unrelated to the dialysis). Pre-dialysis blood samples were taken at the start of the study and at four-week intervals thereafter, and post-dialysis blood samples were obtained after the first and last dialysis. Repeated measure analysis showed that although pre-dialysis blood concentrations of magnesium, potassium and citrate remained within the normal range, there was a significant declining trend over the course of the study. At the same time, pre-dialysis serum bicarbonate levels increased, and significantly more of the patients had a pre-dialysis bicarbonate concentration within the normal range at the end of the study than at the start (15 vs. 8, p=0.001 Chi-square).

In nineteen patients (excluding three patients for whom the type of dialyzer was changed during the study) the dose of dialysis for the first and last dialysis was calculated by the urea reduction ratio (URR) and Kt/V. There was a significant increase in both measurements, without any changes in dialysis time, blood and dialysate flows, or dialyzer used. The URR increased from 68±5.9% to 73±5.3% (p<0.03) and the Kt/V from 1.23±0.19 to 1.34±0.20 (p=0.01) from the first to last dialysis respectively. In conclusion, the citric acid dialysate was well tolerated and intra-dialytic changes in blood chemistries were similar to those seen with regular dialysate. Using dialysate containing citric instead of acetic acid increased the delivered dialysis dose.

These studies are described in more detail below.

Patients and Methods

Two clinical studies compared dialysis using citrate-containing dialysate vs. using standard acetate-containing dialysate. The first, a Crossover study, compared changes in blood chemistry after one dialysis with each of the two dialysate concentrates. A second study involved Exclusive Use of the citrate dialysate for twelve weeks.

An Institutional Review Board approved both studies, and informed consent was obtained from all patients prior to participation. The citrate acid A concentrate was prepared from a dry chemical blend (DRYalysate™, Advanced Renal Technologies, Seattle, Wash.) by mixing it with treated water (AAMI quality) to yield a "citrate concentrate", which contained citrate at a concentration 45 times greater than that which was intended to be used for hemodialysis. The citrate concentrate solution was delivered through the A concentrate input line of Fresenius Model D, E and H and Cobe Centry 3 machines. The B concentrate was prepared from a dry powder, Naturalyte™ (National Medical Care, Rockleigh, N.J.), according to the standard practice at the dialysis units where the studies were done. The acetate A concentrate used was the commercial concentrate, Naturalyte™ 4000 Series Acid Concentrate for Bicarbonate Dialysis (National Medical Care). For both the Crossover and Exclusive Use studies, only the A concentrate was changed, while the B concentrate was the same in both, yielding a final dialysate concentration of 37 mEq/l in all cases.

All blood samples for both studies were analyzed at one laboratory. Serum electrolytes, ionized calcium, urea nitrogen, creatinine, albumin and total protein, were measured in all samples. In addition, serum citrate was measured in thirteen sets of Crossover studies, in hourly samples during seven pairs of dialyses in the Crossover sub-study, and in all Exclusive Use study samples.

Crossover study: The Crossover study was designed to compare single treatment changes in blood chemistry; one treatment using citrate dialysate and the other using regular acetic acid dialysate. The second and third dialyses of the same week were selected for the study. One dialysis was randomly assigned to the citrate concentrate and the other to the patient's regular acetic acid concentrate; the B concentrate used was the same for both dialyses. Changes in blood chemistry using citrate dialysate were compared with those using acetic acid dialysate by measuring pre- and post-dialysis blood concentrations with both dialyses. The composition of the dialysates obtained from the two concentrates is shown in Table 1. For seven patients, in addition to pre- and post-dialysis blood sampling, hourly intradialytic and one-hour post-dialysis blood samples were obtained.

TABLE 1

CHEMICAL COMPOSITION OF THE TWO DIALYSATES, CITRATE AND ACETIC ACID (REGULAR) COMPARED IN THE CROSSOVER STUDY.

| | Citrate Dialysate | Regular Dialysate |
|---|---|---|
| | (in mEq/L except for Dextrose) | |
| Sodium | 137.3 (1) | 137 |
| Chloride | 103.25 to 106.75 | 103.25 to 106.75 |
| Calcium | 2.5 or 3.0 | 2.5 or 3.0 |
| Magnesium | 0.75 | 0.75 |
| Potassium | 0 to 3 | 0 to 3 |
| Dextrose | 2 g/l | 2 g/l |
| Bicarbonate | 37 | 37 |
| Acetate | 0.3 (3) | 4 (2) |
| Citrate | 2.4 (4) | None |

(1) Includes 0.3 mEq/L from sodium acetate.
(2) From acetic acid.
(3) From sodium acetate.
(4) From citric acid.

In the Crossover study, only patients on highflux dialysis using F-60 or F-80 dialyzers (Fresenius Medical Care North America, Lexington, Mass.) were included. Patients with a serum calcium level of less than 9.0 mg/dl or with severe cardiac disease were excluded. A total of 37 sets (74 dialyses) of Crossover studies were performed in 34 patients, with average age of 53.8±15.3 years, of whom nineteen were males and fifteen females. Three patients participated more than once, with a minimum interval between sets of at least two weeks. All treatment variables, including duration, blood and dialysate flows, and dialyzer model were the same for the two dialyses in each set.

Exclusive Use study: After the Crossover study was completed, a second, twelve-week study was conducted using the citrate A concentrate exclusively for 36 consecutive dialysis sessions. Twenty-five patients were enrolled, twenty-two of whom completed the twelve-week study. Three patients dropped out: one was transplanted, one had an extended hospitalization for unrelated reasons, and one moved out of the area.

The average age of the patients was 55.5±13.1 years, there were thirteen males and nine females. Their average time on dialysis was 7.3±4.7 years. Causes of renal failure included diabetes mellitus in four, glomerulonephritis in seven, hypertension in three, and other diseases in eight patients.

Sixteen patients used Fresenius F-80, one Fresenius F-60, two Gambro ALWL20, two Fresenius F-8, and one Baxter CAHP210 dialyzers. With three exceptions, individual patients used the same model dialyzer throughout the study. Pre-dialysis blood samples were obtained at the first dialysis, at four-week intervals, and at the last dialysis. Post-dialysis blood samples were also obtained after the first and last dialysis. Serum electrolytes, ionized calcium, creatinine, urea, proteins and citrate were measured, and pre- and post-dialysis urea and weight changes were used to calculate Kt/V using the Daugirdas 11 formula (Daugirdas, *J. Am. Soc. Nephrol.* 4:1205-1213 (1993)).

Results

Crossover study: All the dialyses with citrate dialysate were uneventful, and no unusual events occurred. Results of the blood analyses are shown in Table 2.

Changes in the concentration of various constituents were calculated by subtracting the post-dialysis concentration from the pre-dialysis concentration. The changes with citrate dialysate were compared to those with acetic acid dialysate. Of sixteen serum constituents measured, the intra-dialytic changes in seven differed significantly with citric acid dialysate compared to acetic acid dialysate. Post-dialysis average concentration of ionized calcium was subnormal, and that of citrate was above normal when using citrate dialysate; post-dialysis magnesium and chloride concentrations were subnormal with both dialysates; and post-dialysis total calcium, sodium, and protein levels were in the normal ranges with both dialysates. FIG. 1 shows the intradialytic and one-hour post-dialysis concentrations of ionized calcium and citrate in fourteen paired treatments with citrate and acetic acid dialysates, both had normalized by one hour after dialysis with citrate dialysate.

Exclusive Use study: No adverse events occurred during twelve weeks of dialysis using only the citrate dialysate. Any trend in pre-dialysis blood chemistry was looked for, and comparing the delivered dose for the first and the last dialyses of the study. Pre-dialysis blood concentrations of all the measured constituents were compared by repeated measured analysis. This analysis fitted growth curve models for the repeated measures, thus enabling an examination of the time trends in response variables while adjusting and estimating the correlation of measures from the same patient. A common correlation coefficient for each variable was also obtained.

TABLE 2

CROSSOVER STUDY AVERAGE PRE- AND POST-DIALYSIS BLOOD CONCENTRATIONS AND CHANGES (Δ = POST-DIALYSIS MINUS PRE-DIALYSIS CONCENTRATION) WITH EACH DIALYSATE. THE DELTA VALUES ARE COMPARED BY STUDENT'S T TEST.

| Blood Test, | Regular Dialysate | | | Citrate Dialysate | | | |
|---|---|---|---|---|---|---|---|
| Units: Ref. Range | Pre | Post | Δ | Pre | Post | Δ | p Value |
| Ionized Calcium, mmol/L: 1.17–1.32 | 1.26 ± 0.10 | 1.25 ± 0.11 | −0.01 ± 0.14 | 1.27 ± 0.11 | 1.10 ± 0.11 | −0.17 ± 0.14 | <0.01 |
| Magnesium, mEq/L: 1.50–1.95 | 1.83 ± 0.25 | 1.37 ± 0.11 | −0.46 ± 0.18 | 1.89 ± 0.24 | 1.31 ± 0.11 | −0.58 ± 0.20 | <0.01 |
| Sodium, mEq/L: 136–145 | 138.1 ± 3.65 | 137.1 ± 2.94 | −1.00 ± 4.16 | 137.3 ± 3.73 | 137.6 ± 3.68 | +0.32 ± 4.02 | 0.01 |
| Chloride, MEq/L: 95–110 | 94.54 ± 5.80 | 94.46 ± 3.43 | −0.09 ± 5.51 | 94.62 ± 4.55 | 93.12 ± 5.18 | −1.5 ± 5.21 | 0.01 |
| Total Calcium, mg/dl: 8.4–10.3 | 9.84 ± 0.87 | 9.76 ± 0.75 | −0.08 ± 0.75 | 9.91 ± 0.86 | 9.15 ± 0.82 | −0.76 ± 0.92 | <0.01 |
| Protein, g/dl: 6.0–8.2 | 7.12 ± 0.52 | 7.57 ± 0.84 | +.44 ± 0.66 | 7.21 ± 0.54 | 7.50 ± 0.80 | +0.30 ± 0.57 | 0.02 |
| Serum Citrate, mg/dl: 1.7–3.0 | 2.21 ± 0.91 | 2.18 ± 0.65 | −0.01 ± 0.43 | 2.35 ± 0.86 | 3.20 ± 0.92 | +0.30 ± 0.63 | 0.01 |
| Hematocrit, %: 39.0–51.0 | 34.87 ± 4.60 | 36.18 ± 4.77 | +1.30 ± 2.68 | 35.40 ± 4.97 | 36.08 ± 5.18 | +0.68 ± 2.67 | 0.06 |
| Potassium, mEq/L: 3.5–5.5 | 5.11 ± 0.95 | 3.36 ± 0.76 | −1.66 ± 0.97 | 5.29 ± 0.74 | 3.45 ± 0.76 | −1.79 ± 0.91 | 0.09 |
| Carbon Dioxide, mEq/L: 23–31 | 22.25 ± 7.23 | 26.08 ± 3.55 | +3.83 ± 6.34 | 21.41 ± 4.25 | 26.62 ± 3.14 | +5.22 ± 3.66 | 0.07 |
| Creatinine, mg/dl: 0.7–1.5 | 8.75 ± 1.64 | 3.12 ± 0.68 | −5.63 ± 1.17 | 8.65 ± 1.65 | 3.09 ± 0.71 | −5.55 ± 1.20 | 0.38 |
| Phosphorus, mg/dl: 2.5–4.7 | 5.46 ± 1.40 | 2.22 ± 0.56 | −3.24 ± 1.16 | 5.34 ± 1.60 | 2.21 ± 1.28 | −3.13 ± 1.71 | 0.30 |
| BUN, mg/dl: 4–22 | 50.94 ± 12.7 | 14.28 ± 4.6 | −36.67 ± 9.8 | 50.51 ± 13.0 | 14.43 ± 5.1 | −36.08 ± 10.0 | 0.37 |
| Albumin, g/dl: 3.3–5.0 | 3.58 ± 0.30 | 3.64 ± 0.43 | +0.06 ± 0.32 | 3.64 ± 0.35 | 3.64 ± 0.46 | 0.00 ± 0.34 | 0.21 |
| AST (GOT), U/L: 0–50 | 12.34 ± 6.88 | +17.66 ± 8.27 | +5.31 ± 3.58 | 13.06 ± 7.28 | 18.15 ± 8.43 | +5.09 ± 3.17 | 0.29 |
| Alkaline Phosphatase, U/L: 30–130 | 106.3 ± 99.6 | 113.8 ± 98.1 | +7.5 ± 9.7 | 108.4 ± 89.2 | 113.2 ± 95.8 | +4.76 ± 12.5 | 0.14 |

This analysis revealed that changes in the concentrations of five variables were significant over the course of the study (Tables 3 and 4).

TABLE 3

PRE-DIALYSIS BLOOD CONCENTRATIONS AT FOUR-WEEK INTERVALS THROUGHOUT THE TWELVE-WEEK STUDY OF EXCLUSIVE USE STUDY WITH CITRATE DIALYSATE. VALUES ARE AVERAGE ± S.D.
Twelve-Week Exclusive Use Study Average Pre-Dialysis Values

| Blood Test, units: Ref. Range | Start | Week 4 | Week 8 | End |
|---|---|---|---|---|
| Magnesium,* mEq/L: 1.50-1.95 | 1.88 ± 0.27 | 1.67 ± 0.22 | 1.68 ± 0.24 | 1.63 ± 0.24 |
| Potassium* mEq/L: 3.5-5.5 | 5.29 ± 0.74 | 4.64 ± 0.70 | 4.79 ± 0.76 | 4.85 ± 0.70 |
| Carbon Dioxide,* mEq/L: 23-31 | 21.55 ± 3.20 | 22.73 ± 3.91 | 22.86 ± 3.14 | 23.50 ± 3.42 |
| AST (GOT)* U/L 0-50 | 10.55 ± 5.93 | 12.14 ± 6.48 | 14.14 ± 7.96 | 14.64 ± 6.51 |
| Serum Citrate,* mg/dl: 1.7-3.0 | 2.08 ± 0.60 | 1.82 ± 0.80 | 1.88 ± 0.70 | 1.60 ± 0.55 |
| Hematocrit, %: 39.0-51.0 | 34.31 ± 3.79 | 35.19 ± 3.72 | 35.37 ± 3.74 | 34.79 ± 4.46 |
| Ionized Calcium, Mmol/L: 1.17-1.32 | 1.24 ± 0.16 | 1.21 ± 0.16 | 1.23 ± 0.13 | 1.23 0.11 |
| Sodium, Meq/L: 136-145 | 136.4 ± 4.55 | 136.9 ± 3.64 | 136.9 ± 4.29 | 137.7 ± 4.05 |
| Chloride, Meq/L: 95-110 | 94.64 ± 4.29 | 95.32 ± 4.62 | 95.32 ± 4.30 | 95.45 ± 4.43 |
| Creatinine, mg/dl: 8.4-10.3 | 9.95 ± 2.11 | 9.19 ± 1.71 | 9.53 ± 1.65 | 9.50 ± 1.99 |
| Total Calcium, mg/dl: 0.7-1.5 | 9.83 ± 1.17 | 9.48 ± 1.06 | 9.69 ± 0.91 | 9.67 ± 0.83 |
| Phosphorus, mg/dl: 2.5-4.7 | 6.30 ± 1.79 | 6.36 ± 2.12 | 6.34 ± 1.74 | 5.78 ± 1.57 |
| BUN, mg/dl: 4-22 | 64.23 ± 20.99 | 55.27 ± 16.47 | 57.45 ± 16.79 | 56.36 ± 17.32 |
| Protein, g/dl: 6.0-8.2 | 6.93 ± 0.59 | 6.97 ± 0.56 | 6.96 ± 0.61 | 6.98 ± 0.48 |
| Albumin, g/dl: 3.3-5.0 | 3.49 ± 0.35 | 3.54 ± 0.37 | 3.54 ± 0.29 | 3.47 ± 0.35 |
| Alkaline Phosphatase, U/L: 30-130 | 81.32 ± 28.63 | 80.59 ± 34.49 | 79.59 ± 34.36 | 81.50 ± 36.02 |

*Indicates a blood value with a significant change (p < 0.05) during the twelve-week study using repeated analysis, see Table 4.

TABLE 4

THE REPEATED MEASURE VALUES FOR THE FIVE VARIABLES THAT EXHIBITED SIGNIFICANT CHANGES OVER THE TWELVE-WEEK EXCLUSIVE USE STUDY.
Twelve-Week Study Results
Summary Results for Linear Growth Curve Models

| | INTERCEPT | | SLOPE | | | CORRELATION | |
|---|---|---|---|---|---|---|---|
| | Est. | 95% CI | Est. | 95% CI | p-value | Est. | 95% CI |
| Magnesium | 1.69 | (1.59, 1.80) | −0.015 | (−0.020, −0.0089) | <0.001 | 0.82 | (+0.68, +0.97) |
| Potassium | 5.11 | (4.79, 5.44) | −0.029 | (−0.051, −0.006) | 0.014 | 0.59 | (+0.38, +0.79) |
| Bicarbonate | 21.67 | (20.27, 23.07) | +.015 | (+0.039, +0.27) | 0.009 | 0.49 | (+0.27, +0.71) |
| AST (GOT) | 10.42 | (7.90, 12.93) | +0.35 | (+0.19, +0.51) | <0.001 | 0.70 | (+0.54, +0.86) |
| Serum Citrate | 2.06 | (1.84, 2.29) | +0.034 | (−0.064, −0.0039) | 0.03 | −0.14 | (−0.25, −0.023) |

In Table 4, to provide a formal analysis and summarization of the twelve-week study, information on the growth curve models was fitted for repeated measures to the data. See, Jennrich and Schluchter, M. D., *Biometrics* 42: 805-820 (1986); and SAS Institute, *SAS/STAT Software Changes and Enhancements Through Release* 6.11, Cary: SAS Institute, Inc. (1996). This enabled an examination of the time trends in the response variables while adjusting and estimating the correlations of the repeated measures from the same patient. For each response variable, a linear growth curve model was fitted with a heterogeneous compound-symmetry covariance structure. Such a model characterizes the mean and covariance structures of the repeated measures in terms of an overall linear trend and a common correlation coefficient. This analysis was performed using the PROC MIXED Procedure in SAS (SAS Institute, *SAS/STAT Software Changes and Enhancements Through Release* 6.11, Cary: SAS Institute, Inc. (1996).

In this study, and as shown in Tables 3 and 4, the concentrations of the other eleven constituents measured, including total and ionized calcium and sodium, remained stable and unchanged. The decrease in potassium and increase in AST (GOT) levels were minor, and remained well within the normal ranges. The most notable changes encountered were decreases in both serum magnesium and citrate, along with increase in bicarbonate concentrations. Pre-dialysis average bicarbonate concentration improved from a subnormal level at the start to a normal level at the end of the study (p<0.01). At the start of the study, fourteen of twenty two patients had a pre-dialysis bicarbonate concentration of less than 23 mEq/l (lower limit of normal); at the end of study bicarbonate level had normalized in all but seven patients (p<0.001, chi-square).

Dose of Dialysis: Every attempt was made to keep the dialysis treatment variables constant, but in three patients the dialyzer type, was changed during the study. Data from these three patients were excluded, and the URR and Kt/V values for the remaining nineteen patients are shown in FIGS. 2 and 3. The delivered dose of dialysis was significantly higher for the last dialysis compared to the first dialysis of the study. Analysis of dialysis variables showed that blood flow, dialysis time and number of reuses for the processed dialyzers for these two treatments were comparable (Table 5), dialyzer type remained unchanged for each patient, and dialysate flow was constant at 500 ml/min.

TABLE 5

DIALYSIS TREATMENT VARIABLES FOR THE FIRST AND LAST TREATMENT OF THE TWELVE-WEEK EXCLUSIVE USE STUDY. VALUES ARE MEAN + S.D.

|  | Start of Study | End of Study |
| --- | --- | --- |
| Urea Reduction Ratio | 68% ± 5.9% | 73% ± 5.3% |
| Kt/V | 1.23 ± 0.19 | 1.34 ± 0.20 |
| Blood Flow (ml/min) | 368 ± 47.7 | 375 ± 41.2 |
| Dialysis Time (hrs) | 3.9 ± 0.39 | 3.9 ± 0.48 |
| Dialyzer Reuses, number | 8.55 ± 11.6 | 10.9 ± 9.9 |

Discussion

The new dialysate containing citric acid was well tolerated, and no untoward effects were seen during either study. The amount of citrate derived from citric acid was 2.4 mEq/l, which is lower than the 4 mEq/l of acetate typically derived from acetic acid with current dialysate. The blood citrate level was slightly above the upper limit of normal during and immediately after dialysis, falling to within the normal range by one hour after dialysis. This suggests the citric acid load from the dialysate was easily metabolized. During the course of the twelve-week study the pre-dialysis citrate concentration did not increase, showing that there was no accumulation of citrate over time. In fact, the trend was a statistically significant decrease in pre-dialysis citrate concentration during the study.

The significant pre- to post-dialysis decline in total and ionized calcium levels during citrate dialysis (Table 2) presumably is due to binding with citrate, a well-known effect. This decline was more pronounced in patients using dialysate containing 2.5 mEq/l of calcium compared with those on a 3.0 mEq/l calcium bath. However, recovery of the calcium levels by one hour post-dialysis in the Crossover study and by the next dialysis in the Exclusive Use study shows that calcium repletion from body stores and/or from the dissociation of calcium citrate complex is sufficient to maintain the serum calcium level within the normal range.

The magnesium concentration in the dialysate of 0.75 mEq/l resulted in a significant decline in post-dialysis serum magnesium levels with both dialysates. This decline was more pronounced with citrate dialysate, and throughout the twelve-week study the pre-dialysis magnesium level stayed low. Magnesium has a strong affinity for citrate and easily complexes with it (Janssen et al., *Blood Purif.* 12:308-316 (1994)). The lower dialysate magnesium should have favored removal of the complexed molecule during dialysis, producing the decline in the serum magnesium. Use of a higher level of magnesium in the dialysate (>0.75 mEq/l) should prevent any undesired decrease in magnesium. Alternatively, this effect could be helpful by reducing magnesium accumulation if magnesium-containing phosphate binders are used.

The trend of an increase in pre-dialysis serum bicarbonate levels observed in this study is encouraging. Persistent metabolic acidosis in dialysis patients has been associated with increased protein catabolism (Reaich et al., *Am. J. Physiol.* 265:E230-E235 (1993), increased turnover of beta$_2$ microglobulin (Sonikian et al., *J. Am. Soc. Nephrol.* 7:350-356 (1996), bone metabolism problems (Lin et al., *ASAIO J.* 40:M440-M444 (1994) and abnormal muscle functions (Guest et al., *J. Am. Soc. Nephrol.* 8:236A (1997) (Abstract). Correction of metabolic acidosis has been attempted either by increasing dialysate bicarbonate concentration (Ahmad et al., *Trans. Am. Soc. Artif Intern. Organs* 26:318-321 (1980) or by prescribing oral bicarbonate (Brady and Hasbargen, *Am. J. Kid. Dis.* 31:35-40 (1998), but both approaches have associated practical and clinical problems. Citrate is metabolized in liver and muscle to produce bicarbonate, and patients getting massive blood transfusions are known to develop alkalosis as a result of the increased citrate load (Dzik and Kirkley, *Trans. Med. Rev.* 2:76-94 (1988). Thus, citrate metabolism alone may explain the increase in serum bicarbonate level. However, increased intradialytic bicarbonate transfer from the dialysate to the blood might also be a factor as the result of a possible effect of citric acid on the dialyzer membrane (see below). The improvement in bicarbonate during the Exclusive Use study may have been a result of citrate metabolism, increased influx of bicarbonate during dialysis, or a combination of these two effects.

The significant increase in delivered dose of dialysis seen at the end of the twelve-week study was not a result of any increase in blood or dialysate flows, dialysis time, or change in dialyzers—known factors influencing the dose. It is possible that the increased removal of urea (increased dose) may be attributable to the presence of citrate in the dialysate. We postulate that by binding, with calcium, dialysate citrate provides a local anticoagulant effect at the dialyzer membrane level. This effect may help to preserve membrane permeability and keep the capillary fibers patent. This could explain the observed increase in transfer of solutes such as urea and bicarbonate between dialysate and blood. The study was not designed to address this issue and so there is no conclusive evidence to support this hypothesis. However, if confirmed by further study, this effect of citrate on improving dialysis efficiency could benefit by making dialysis more efficient.

In conclusion, these results show that a citrate dialysate is safe and can be used without associated technical or clinical problems. No modification of the dialysis machine is needed, and a citric acid concentrate can be substituted for the current acetic acid concentrate. These studies also demonstrate an increase in urea transfer with the citrate dialysate. If this dialysate can be shown to have similar effects on other molecules, then its use will increase dialyzer efficiency in the removal of uremic toxins.

From the foregoing it will be appreciated that, although specific embodiments of the invention have been described herein for purposes of illustration, various modifications may be made without deviating from the spirit and scope of the invention.

What is claimed is:

1. A method of performing dialysis on a patient in need thereof, wherein the method comprises:
   a) performing the dialysis in the absence of direct administration of anticoagulant to the patient; and
   b) performing the dialysis in a dialyzer with a dialysate composition comprising citrate at a concentration ranging from greater than 2.4 to 20 mEq/L, calcium at a concentration ranging from 2.5 to 5 mEq/L, magnesium at a concentration ranging from 0.75 to 2 mEq/L, sodium bicarbonate at a concentration ranging from about 25 to about 40 mEq/L and a buffering anion selected from the group consisting of acetate, in the form of an acetate salt, and lactate, in the form of a lactate salt, or a mixture thereof, at a concentration ranging from about 0.001 to about 4.0 mEq/L.

2. The method of claim 1 wherein the patient is suffering from acute kidney failure.

3. The method of claim 1 wherein the patient has an intolerance to heparin.

4. The method of claim 1 wherein the patient has an antibody to heparin.

5. The method of claim 1 wherein the patient has a risk of bleeding from the use of direct administration of anticoagulant.

6. The method of claim 1 wherein the patient has chronic acidosis.

7. The method of claim 1 wherein the dialysis is performed in the absence of direct administration of heparin.

8. The method of claim 1 wherein the dialysis results in an increased urea transfer from the patient's blood to the dialysate in comparison to the level of urea transfer obtained with dialysate compositions that do not contain citrate.

9. The method of claim 1 wherein the dialysis results in an increased level of bicarbonate concentration in the patient's blood in comparison to the level of bicarbonate concentration obtained with dialysate compositions that do not contain citrate.

10. The method of claim 1 wherein the dialysis results in an increased effective flow of the patient's blood through the dialyzer in comparison to the effective rate of blood flow obtained with dialysate compositions that do not contain citrate.

11. The method of claim 1 wherein the dialysate composition further comprises sodium chloride at a concentration ranging from about 110 to about 140 mEq/L.

12. The method of claim 1 wherein the citrate is in the form of citric acid, sodium dihydrogen citrate, disodium hydrogen citrate, trisodium citrate, potassium dihydrogen citrate or dipotassium hydrogen citrate, or any mixture thereof.

13. The method of claim 1 wherein the dialysis results in an increased re-use of the dialyzer in comparison to the re-use of a dialyzer obtained with dialysate compositions that do not contain citrate.

14. A method of performing dialysis on a patient in need thereof, wherein the patient does not have a high level of heparin within the patient's blood during the time of dialysis and wherein the method comprises performing the dialysis in a dialyzer with a dialysate composition comprising citrate at a concentration ranging from greater than 2.4 to 20 mEq/L, calcium at a concentration ranging from 2.5 to 5 mEq/L, magnesium at a concentration ranging from 0.75 to 2 mEq/L, sodium bicarbonate at a concentration ranging from about 25 to about 40 mEq/L and a buffering anion selected from the group consisting of acetate, in the form of an acetate salt, and lactate, in the form of a lactate salt, or a mixture thereof, at a concentration ranging from about 0.001 to about 4.0 mEq/L.

15. The method of claim 14 wherein the patient is suffering from acute kidney failure.

16. The method of claim 14 wherein the dialysis is performed in the absence of systemic administration of heparin.

17. The method of claim 14 wherein the dialysis results in an increased urea transfer from the patient's blood to the dialysate in comparison to the level of urea transfer obtained with dialysate compositions that do not contain citrate.

18. The method of claim 14 wherein the dialysis results in an increased level of bicarbonate concentration in the patient's blood in comparison to the level of bicarbonate concentration obtained with dialysate compositions that do not contain citrate.

19. The method of claim 14 wherein the dialysis results in an increased flow of the patient's blood through the dialyzer in comparison to rate of blood flow obtained with dialysate compositions that do not contain citrate.

20. The method of claim 14 wherein the dialysate composition further comprises sodium chloride at a concentration ranging from about 110 to about 140 mEq/L.

21. The method of claim 14 wherein the citrate is in the form of citric acid, sodium dihydrogen-citrate, disodium hydrogen citrate, trisodium citrate, potassium dihydrogen citrate or dipotassium hydrogen citrate, or any mixture thereof.

22. The method of claim 14 wherein the dialysis results in an increased re-use of the dialyzer in comparison to the re-use of the dialyzer obtained with dialysate compositions that do not contain citrate.

23. A method of performing dialysis on a patient in need thereof, wherein the method comprises:
   (a) performing the dialysis in the absence of direct administration of anticoagulant to the patient; and
   (b) performing the dialysis in a dialyzer with a dialysate composition comprising:
   citrate at a concentration ranging from greater than 2.4 to 20 mEq/L;
   calcium at a concentration ranging from 2.5 to 5 mEq/L;
   magnesium at a concentration ranging from 0.75 to 2 mEq/L;
   a buffering anion selected from the group consisting of acetate, in the form of an acetate salt, and lactate, in the form of a lactate salt, or a mixture thereof, at a concentration ranging from about 0.001 to about 4.0 mEq/L;
   sodium bicarbonate at a concentration ranging from about 25 to about 40 mEq/L; and
   sodium chloride at a concentration ranging from about 110 to about 140 mEq/L;
   wherein the dialysis results in one or more of the following:
   (1) an increased urea transfer from the patient's blood to the dialysate;
   (2) an increased level of bicarbonate concentration in the patient's blood;
   (3) an increased effective flow of the patient's blood through the dialyzer; or
   (4) an increased re-use of the dialyzer;
   in comparison to dialysis results obtained with dialysate compositions that do not contain citrate.

24. The method of claim 23 wherein the dialysis is performed in the absence of direct administration of heparin.

25. A method of performing dialysis on a patient in need thereof, wherein the method comprises performing the dialysis in a dialyzer with a dialysate composition comprising citrate at a concentration ranging from greater than 2.4 to 20 mEq/L, calcium at a concentration ranging from 2.5 to 5 mEq/L, magnesium at a concentration ranging from 0.75 to 2 mEq/L, sodium bicarbonate at a concentration ranging from about 25 to about 40 mEq/L and a buffering anion selected from the group consisting of acetate, in the form of an acetate salt, and lactate, in the form of a lactate salt, or a mixture thereof, at a concentration ranging from about 0.001 to about 4.0 mEq/L; wherein the patient has one or more of the following:
  a) a risk of bleeding from the use of systemic anticoagulation;
  b) an antibody to heparin;
  c) intolerance to heparin; and
  d) chronic acidosis.

26. The method of claim 25 wherein the dialysate composition further comprises sodium chloride at a concentration ranging from about 110 to about 140 mEq/L.

27. The method of claim 26 wherein the dialysis results in one or more of the following:
  (1) an increased urea transfer from the patient's blood to the dialysate;
  (2) an increased level of bicarbonate concentration in the patient's blood;
  (3) an increased effective flow of the patient's blood through the dialyzer; or
  (4) an increased re-use of the dialyzer;
  in comparison to dialysis results obtained with dialysate compositions that do not contain citrate.

* * * * *